Dec. 27, 1966 F. W. ANDERSON Plant Pat. 2,695
ALMOND TREE
Filed Sept. 7, 1965
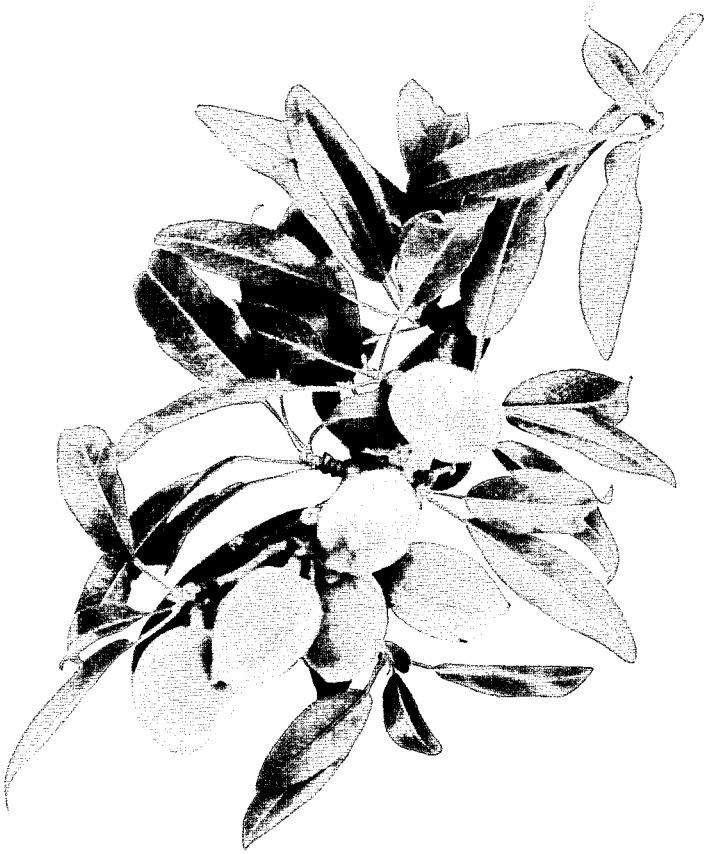
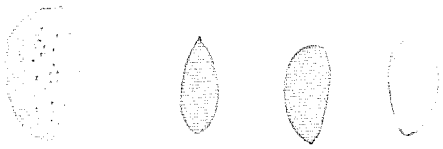
INVENTOR
Frederic W. Anderson
By
Webster & Webster
ATTORNEYS United States Patent Office Plant Pat. 2,695
Patented Dec. 27, 1966

2,695
ALMOND TREE

Frederic W. Anderson, Merced, Calif., assignor to Arthur Bright, Le Grand, Calif.

Filed Sept. 7, 1965, Ser. No. 485,659
1 Claim. (Cl. Plt.—30)

This invention relates to a new and distinct variety of almond tree which bears nuts having relatively small kernels which are intermediate in appearance between those of the unpatented Nonpareil and Mission varieties. As the size and shape of the kernels are such that they will meet the requirements of confectionery manufacturers, the present variety of almond tree can be advantageously commercially grown.

The present variety of almond tree is characterized, as to novelty, by the regular and heavy production of small but well distributed nuts having kernels which are thinner and smaller than the Mission; the nuts in other respects somewhat resembling the Mission in that they have a relatively hard, well-sealed shell, and kernels of similar color. Further, there are very few doubles or otherwise defective kernels.

An additional important and novel characteristic of the present variety of almond tree is that it has proved intercompatible with all other almond varieties with which it has been tested, including the unpatented Nonpareil and Mission and the United States plant patented varieties of Ruby (No. 1,698), Emerald (No. 2,208), Empire (No. 2,367), Ripon (No. 2,379), Butte (No. 2,380), Norman (No. 2,426), Yosemite (No. 2,534), and Wawona (No. 2,548).

Other characteristics of the present variety are a blooming period two to five days after the Mission, and a harvest period between the Nonpareil and Mission.

The herein claimed variety of almond tree was originated by me in my experimental orchard located near Le Grand, Merced County, California, during the course of a long and continuing plant breeding program seeking improved varieties of fruits and nuts, including almonds. Such origination was accomplished as follows:

I first gathered seed from the tree of an unnamed variety that was a late blooming double-flowered mutation of Nonpareil; such seed parent tree having been in a block of Mission trees, and presumably most of its flowers were fertilized by pollen from such Mission trees.

The seed, as so gathered, was planted and the resutlant seedlings grown under continuing observation. The present variety is one of such seedlings, and when it came into bearing I recognized its novel and distinctive characteristics and, therefore, selected it for subsequent reproduction.

Thereafter, I asexually reproduced the variety in my experimental orchard, located as aforesaid, by top-working on a pollenizer row of approximately one-quarter mile in length; such reproductions, together with a later planted block of nursery trees, having run true to the seedling parent in all respects.

The drawing comprises an illustration, by photographic reproduction in color, of a twig with leaves and in-hull nuts; a nut with the hull removed; a kernel from one edge; a kernel from one side; and a kernel cut to expose the meat.

Referring now more specifically to the botanical details of this new and distinct variety of almond tree, the following is an outline description thereof; all major color plate identifications being by reference to Maerz and Paul Dictionary of Color; except where common terms of color definition are employed:

Tree:
- *Density.*—Open.
- *Size.*—Medium.
- *Vigor.*—Vigorous.

Trunk:
- *Form.*—Medium.
- *Texture.*—Medium.

Branches:
- *Form.*—Medium.
- *Texture.*—Medium.
- *Lenticels.*—Medium number; medium size.
- *Branching habit.*—Medium.
- *Color.*—New wood—brown to gray. Mature wood—gray.

Foliage: Quantity—abundant.

Leaves:
- *Size.*—Medium to small. Average length—2½". Average width—13/16".
- *Shape.*—Abruptly pointed.
- *Thickness.*—Medium.
- *Texture.*—Smooth.
- *Margin.*—Crenate.
- *Petiole.*—Length—medium; average, ⅞". Thickness—medium.
- *Glands.*—Average number and position—2 to 3 on petiole near base of blade. Alternate; small.
- *Color.*—Top side—medium green (23–L–7). Under side—lighter green (22–L–7).

Bloom:
- *Amount of bloom.*—Heavy.
- *Color.*—White.
- *Blooming period.*—Late—about 2 to 5 days after Mission.

Crop:
- *Bearing.*—Regular bearer.
- *Productivity.*—Heavy.
- *Distribution of nuts on tree.*—Well distributed.
- *Harvest period.*—Medium—between Nonpareil and Mission.
- *Tenacity.*—Hangs well on tree; easy to harvest; easy to hull.

Hull:
- *Outer surface.*—Smooth.
- *Form.*—Regular.
- *Thickness.*—Thick.
- *Flesh.*—Tough.
- *Suture.*—Flat.
- *Color.*—Light green (22–K–6) with silvery sheen.
- *Dehiscence.*—Opens freely.
- *Splitting.*—At ripening, splits down ventral suture.

Nut:
- *Size.*—Medium to small. Average length—1¼". Average thickness—7/16".
- *Form.*—Length/width—ovate. Width/thickness — Medium.
- *Shell.* Soft; smooth. Outer shell—hard. Inner shell—hard to soft; well sealed.
- *Color.*—Straw (11–G–5).
- *Pits.*—Small; shallow; irregular.
- *Base.*—Square to slightly ventrally oblique.
- *Stem scar.*—Large.
- *Apex.*—Acute; tip recurved slightly.
- *Wing.*—Narrow; thin; tapered toward base.
- *Inner surface.*—Medium colored.
- *Ventral streak.*—Dark; narrow; short.
- *Percentage of kernel to nut on average sample.*—50 percent.

Kernel:

*Size.*—Medium to small.—Average length—$1\frac{3}{16}''$. Average width—$\frac{3}{8}''$. Average thickness—$\frac{1}{4}''$.

*Kernels per ounce on average sample.*—33 to 39.

*Form.*—Length/width—ovate. Width/thickness — medium to flat.

*Base.*—Square to slightly ventrally oblique.

*Stem scar.*—Small; obtuse.

*Apex.*—Obtuse.

*Plumpness.*—Smooth.

*Pellicle.*—Medium.

*Pubescence.*—Medium.

*Color.*—Medium light brown (14–H–11).

*Number of doubles.*—Very few.

*Defective kernels.*—Very few.

*Flavor.*—Normal.

*Quality.*—Good.

The tree and its nuts herein described may vary in slight detail due to climatic and soil conditions under which this variety may be grown; the present description being of the variety as grown in the Central Valley of California.

The following is claimed:

A new and distinct variety of almond tree, as illustrated and described, characterized by a tree which blooms two to five days after the Mission and is in harvest between the Nonpareil and Mission; the tree being a regular and productive bearer of small, well sealed nuts having thin, flat kernels of confectionery type.

No references cited.

ABRAHAM G. STONE, *Primary Examiner.*

R. E. BAGWILL, *Assistant Examiner.*